US00PP13739P29

(12) United States Plant Patent
Fell, Jr.

(10) Patent No.: US PP13,739 P2
(45) Date of Patent: Apr. 29, 2003

(54) DRACAENA PLANT NAMED 'HAWAIIAN SUNSHINE'

(76) Inventor: David N. Fell, Jr., 2191 Ainaola Dr., Hilo, HI (US) 96720

( * ) Notice: Subject to any disclaimer, the term of this patent is extended or adjusted under 35 U.S.C. 154(b) by 0 days.

(21) Appl. No.: 10/103,952

(22) Filed: Mar. 22, 2002

(51) Int. Cl.[7] ..... A01H 5/00

(52) U.S. Cl. ..... Plt./383
(58) Field of Search ..... Plt./383

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Dracaena plant named 'Hawaiian Sunshine', characterized by its compact, upright and outwardly arching growth habit; narrow and short leaves; and dark green and light green variegated glossy leaves.

1 Drawing Sheet

BOTANICAL CLASSIFICATION/CULTIVAR DESIGNATION

Dracaena deremensis cultivar Hawaiian Sunshine.

BACKGROUND OF THE INVENTION

The present invention relates to a new and distinct cultivar of Dracaena plant, botanically known as *Dracaena deremensis*, and hereinafter referred to by the cultivar name Hawaiian Sunshine.

The new cultivar was discovered by the Inventor in a controlled environment in Hilo, Hi. as a naturally-occurring whole plant mutation of the *Dracaena deremensis* cultivar Hilo Girl, not patented. The new Dracaena was observed as a single plant in a group of plants of 'Hilo Girl' Feb. 1, 2000. This plant was selected on its unique leaf variegation pattern as plants of the cultivar Hilo Girl do not have variegated leaves.

Asexual propagation of the new cultivar by cuttings at Hilo, Hi. since Sep. 1, 2000, has shown that the unique features of this new Dracaena plant are stable and reproduced true to type in successive generations of asexual propagation.

The new Dracaena has not been observed under all possible environmental conditions. The phenotype may vary somewhat with variations in environment such as temperature and light intensity, without, however, any variance in genotype.

SUMMARY OF THE INVENTION

The following traits have been repeatedly observed and are determined to be the unique characteristics of'Hawaiian Sunshine'. These characteristics in combination distinguish 'Hawaiian Sunshine' as a new and distinct cultivar:

1. Compact, upright and outwardly arching growth habit.
2. Narrow and short leaves.
3. Dark green and light green variegated glossy leaves.

The new Dracaena can be compared to plants of variegated Dracaena fragrans 'Massangeana', not patented. However in side-by-side comparisons conducted in Hilo, Hi, plants of the new Dracaena had shorter and narrower leaves. In addition, leaves of plants of the new Draceana had glossy leaves whereas leaves of plants of the cultivar Massangeana had dull leaves.

DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Dracaena.

The photograph at the top of the sheet comprises a side perspective view of a typical potted plant of 'Hawaiian Sunshine'.

The photograph at the bottom of the sheet comprises a top perspective view of a typical plant of 'Hawaiian Sunshine'.

DETAILED BOTANICAL DESCRIPTION

The aforementioned photographs and following observations and measurements describe plants grown in Hilo, Hi. in a polyethylene-covered greenhouse during the winter with day temperatures ranging from 18 to 28° C., night temperatures ranging from 13 to 22° C., and light levels about 4,000 foot-candles. The photographs and the description were taken about 36 weeks after planting. Plants were grown in 25-cm containers. In the description, color references are made to The Royal Horticultural Society Colour Chart, 1995 Edition, except where general terms of ordinary dictionary significance are used.

Botanical classification: *Dracaena deremensis* cultivar Hawaiian Sunshine.

Parentage: Naturally-occurring whole plant mutation of the *Dracaena deremensis* cultivar Hilo Girl, not patented.

Propagation:

*Method.*—By cuttings.

*Time to initiate roots.*—Summer: About 14 days at 28° C. Winter: About 21 days at 20 ° C.

*Time to produce a rooted young plant.*—Summer: About 30 days at 28° C. Winter: About 36 days at 20° C.

*Root description.*—Numerous, thick and fibrous; close to 179D in color with whitish apices.

Plant description:

*Plant shape.*—Compact, upright and outwardly spreading; columnar.

*Plant height.*—About 67.5 cm from soil level to top of leaf plane.

*Plant diameter or spread.*—About 58 cm.

*Plant vigor.*—Moderate.

*Growth rate.*—Relatively rapid.

*Stem diameter, at base.*—About 2.5 cm.

*Foliage description.*—relatively short and narrow; outwardly arching; decurrent, sessile. Quantity of leaves per finished plant: About 41. Arrangement: Alternate. Shape: Linear, narrow. Apex: Narrowly acute. Margin: Entire. Texture, upper and lower surfaces: Leathery, smooth, glabrous. Luster, upper and lower surfaces: Glossy. Venation pattern: Parallel. Length: About 43 cm. Width: About 6.5 cm. Color: Longitudinally variegated. Young and fully expanded leaves, upper surface: Margins are dark green, darker than 147A. Central area with light green longitudinal stripes, 144A. Young and fully expanded leaves, lower surface: Margins are dark green, darker than 146A to close to 147A. Central area with light green longitudinal stripes, close to 144A. Venation, upper and lower surfaces: Same as lamina coloration.

Flower description: Flowers have not been observed on plants of the new Dracaena.

Disease/pest resistance: Under commercial conditions, resistance to pathogens and pests common to Dracaenas has not been observed.

Temperature tolerance: Plants of the new Dracaena have been observed to tolerate temperatures from 10 to 30° C.

It is claimed:

1. A new and distinct cultivar of Dracaena plant named 'Hawaiian Sunshine' as illustrated and described.

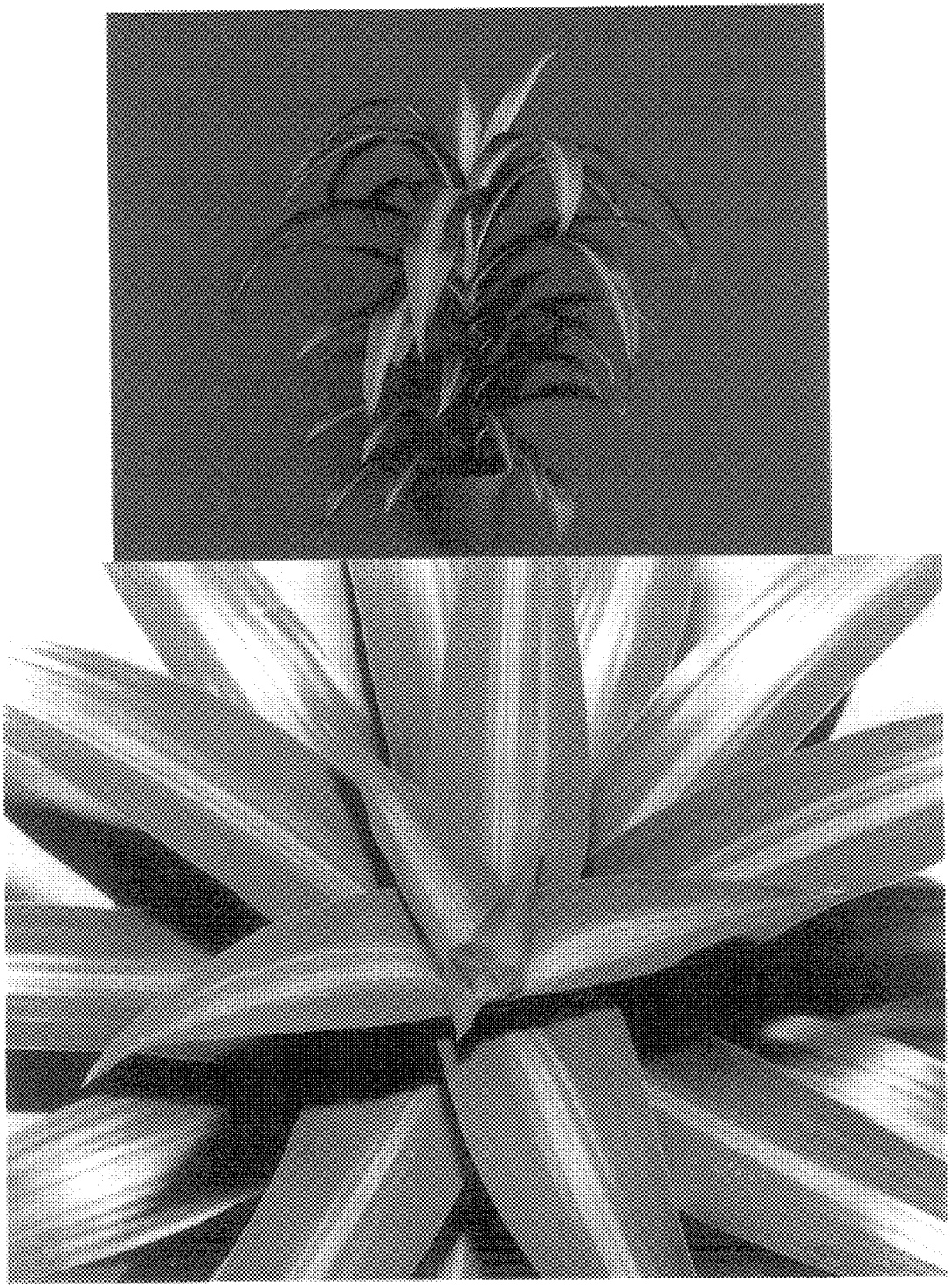

* * * * *